US007655800B2

(12) United States Patent
Chase et al.

(10) Patent No.: US 7,655,800 B2
(45) Date of Patent: Feb. 2, 2010

(54) CRYSTALLINE 1H-IMIDAZO[4,5-B]PYRIDIN-5-AMINE, 7-[5-[(CYCLOHEXYLMETHYLAMINO)-METHYL]-1H-INDOL-2-YL]-2-METHYL, SULFATE (1:1), TRIHYDRATE AND ITS PHARMACEUTICAL USES

(75) Inventors: Charles E. Chase, Londonderry, NH (US); Ikuo Kushida, Tsukuba (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 42 days.

(21) Appl. No.: 11/344,534

(22) Filed: Feb. 1, 2006

(65) Prior Publication Data

US 2006/0194833 A1    Aug. 31, 2006

Related U.S. Application Data

(60) Provisional application No. 60/648,701, filed on Feb. 2, 2005.

(51) Int. Cl.
C07D 471/04    (2006.01)
A61K 31/437    (2006.01)
(52) U.S. Cl. ........................ 546/118; 514/303
(58) Field of Classification Search ............... 546/118; 514/303
See application file for complete search history.

(56) References Cited

U.S. PATENT DOCUMENTS

| | | | | |
|---|---|---|---|---|
| 6,860,940 | B2 * | 3/2005 | Segelke et al. | 117/68 |
| 7,015,041 | B2 * | 3/2006 | Santarsiero et al. | 436/4 |
| 7,052,545 | B2 * | 5/2006 | Quake et al. | 117/68 |
| 7,195,670 | B2 * | 3/2007 | Hansen et al. | 117/68 |
| 7,214,540 | B2 * | 5/2007 | DeLucas et al. | 436/86 |
| 7,229,500 | B2 * | 6/2007 | Haushalter et al. | 117/95 |
| 2004/0186127 | A1 | 9/2004 | Daun et al. | |

FOREIGN PATENT DOCUMENTS

WO    WO 03/057696 A1    7/2003
WO    WO 2004/063336 A2    7/2004

OTHER PUBLICATIONS

Gatterman, Ludwig The Practical Methods of Organic Chemistry 1896, MacMillan: New York, pp. 1-14.*
Berge "Pharmaceutical Salts" Journal of Pharmaceutical Sciences 1977, 66, 1-19.*
Morissette et. al. "High-throughput crystallization: polymorphs, salts, co-crystals and solvates of pharmaceutical solids" Advanced Drug Delivery Reviews 2004, 56, 275-300.*
Pudipeddi et. al. "Trends in Solubility of Polymorphs" Journal of Pharmaceutical Sciences, May 2005, 94, 929.*
Hillery et. al. Drug delivery and targeting for pharmacists and pharmaceutical scientists Taylor and Francis 2001, p. 29.*
International Search Report, Dated May 24, 2006.
Brown, Joan Heller, et al., "Muscarinic Receptor Agonists and Antagonists," *Goodman and Gilman's The Pharmacological Basis of Therapeutics*, Tenth Edition, A. Gilman, J. Hardman and L. Limird, eds., McGraw-Hill Press, pp. 155-173, 2001.
*Remington's Pharmaceutical Sciences*, Sixteenth Edition, E. W. Martin (Mack Publishing Co., Easton, Pa., 1980), Table of Contents.
Tak, Paul P. et al., NF-κB: a key role in inflammatory diseases—NF-κB in Defense and Disease, *The Journal of Clinical Investigation*, Jan. 2001, vol. 107, pp. 7-11.

* cited by examiner

*Primary Examiner*—Rita J Desai
*Assistant Examiner*—David K O'Dell
(74) *Attorney, Agent, or Firm*—Nixon Peabody LLP; Jeffrey N. Townes

(57) ABSTRACT

The invention relates to crystalline 1H-Imidazo[4,5-b]pyridin-5-amine, 7-[5-[(cyclohexylmethylamino)-methyl]-1H-indol-2-yl]-2-methyl, sulfate (1:1), trihydrate, E6070, its method of preparation, and its therapeutic uses. Pharmaceutical compositions containing crystalline E6070 and a pharmaceutically acceptable carrier represent one embodiment of the invention. The invention also relates to methods for treating an inflammatory disorder, an autoimmune disorder, or a proliferative disorder comprising the step of administering to a patient in need thereof a therapeutically effective amount of crystalline E6070.

16 Claims, 13 Drawing Sheets

CRYSTALLINE 1H-IMIDAZO[4,5-B]PYRIDIN-5-AMINE, 7-[5-[(CYCLOHEXYLMETHYLAMINO)-METHYL]-1H-INDOL-2-YL]-2-METHYL, SULFATE (1:1), TRIHYDRATE AND ITS PHARMACEUTICAL USES

FIELD OF INVENTION

This invention relates to 1H-Imidazo[4,5-b]pyridin-5-amine, 7-[5-[(cyclohexylmethylamino)-methyl]-1H-indol-2-yl]-2-methyl, sulfate (1:1), trihydrate, (E6070), in its crystalline form. Possessing the ability to inhibit NF-κB activation through inhibition of the IKKβ protein kinase E6070 is potent therapeutic agent for the treatment of inflammatory, autoimmune and proliferative diseases and disorders.

BACKGROUND OF INVENTION

Inflammation is a process resulting from the dilation and increased permeability of blood vessels at site of injury or infection. Chemokines and cytokines released at the site increase the expression of cell surface proteins on endothelial cells, allowing circulating leukocytes to stick to the vessel wall and migrate to the site of injury/infection within the tissue. These cell surface proteins, termed "cell adhesion molecules" allow the interaction between the leukocytes and the endothelial cells, and mediate the migration of leukocytes into the tissue. Additionally, cell adhesion molecules are required for many of the cell-to-cell interactions in the inflammatory and immune responses. There are three classes of adhesion molecules: selectins, integrins and immunmoglobulin-related proteins which can be expressed on leukocytes and endothelial cells. Several of the adhesion molecules, including E-selectin and ICAM, are induced by cytokines such as IL-1 and TNF, and their expression is mediated by the transcriptional factor, NF-κB.

Sustained or inappropriate expression of adhesion molecules can lead to inflammatory or autoimmune disorders. Exaggerated expression of E-selectin and/or ICAM can result in chronic inflammation and has been associated with several inflammatory or autoimmune disorders. Therefore, inhibitors of cell adhesion molecules may be useful for the treatment of these diseases.

Inflammatory and autoimmune diseases are not well managed by current therapy and developments of better drugs are widely pursued. For example, rheumatoid arthritis is a state of chronic inflammation within the joint characterized by cartilage and bone destruction. Traditional therapies for inflammatory or autoimmune disease, such as rheumatoid arthritis, include nonsteroidal anti-inflammatory drugs and salicylates, gold compounds, hydroxychloroquine, sulfasalazine, corticosteroids, oral penicillamines, and cytotoxic or immunosuppressive drugs. However, many of these therapies are not always sufficiently effective and have resulted in serious side effects. More recently, injectable forms of TNFα neutralizing proteins have been successfully marketed for the treatment of rheumatoid arthritis and Crohn's Disease, however, an orally available inhibitor has not been developed for these inflammatory or autoimmune diseases.

Able to inhibit NF-κB activation through inhibition of the IKKβ protein kinase, 1H-Imidazo[4,5-b]pyridin-5-amine, 7-[5-[(cyclohexylmethylamino)-methyl]-1H-indol-2-yl]-2-methyl (ER-807447) is a potent anti-cytokine/anti-inflammatory agent. Published PCT application WO 2004/06336 A2 and published U.S. application 2004/0186127 A1 disclose ER-807447 as a member of a novel class of deazapurine therapeutic agents having antiflammatory/autoimmune and anti-proliferative effects (both of these published applications are incorporated here by reference). These deazapurine therapeutic agents are orally available and are free of serious side effects.

Although therapeutic efficacy is the primary concern for a therapeutic agent, the salt and crystal form of a drug candidate can be critical to its development. Each salt or each crystalline form (polymorph) of a drug candidate can have different physical and chemical properties, for example, solubility, stability, or the ability to be reproduced. These properties can impact the ultimate pharmaceutical dosage form, the optimization of manufacturing processes, and absorption in the body. Moreover, finding the most adequate form for further drug development, can reduce the term and the cost of that development.

Obtaining pure crystalline forms is extremely useful in drug development. It permits better characterization of the drug candidate's chemical and physical properties. The crystalline form may possess more favorable pharmacology than the amorphous form or be easier to process. It may also possess more storage stability.

The solid state physical properties of a drug candidate influence its selection as a pharmaceutical active ingredient and the choice of form for its pharmaceutical composition. One such physical property, for example, is the flowability of the solid, before and after milling. Flowability affects the ease with which the material is handled during processing into a pharmaceutical composition. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate. Another important solid state property of a pharmaceutical compound is its dissolution rate in aqueous fluid. The rate of dissolution of an active ingredient in a patient's gastrointestinal fluid may have therapeutic consequences since it impacts the rate at which an orally-administered active ingredient may reach the patient's bloodstream.

These practical physical properties are influenced by the conformation and orientation of molecules in the unit cell of the crystalline compound. The crystalline (or polymorphic) form often has different thermal behavior different from the amorphous material or another polymorphic form. Thermal behavior is measured in the laboratory by such techniques as capillary melting point, thermogravimetric analysis (TGA) and differential scanning calorimetry (DSC) and may be used to distinguish some polymorphic forms from others. A crystalline form or a particular polymorphic form generally possesses distinct crystallographic and spectroscopic properties detectable by powder X-ray diffraction (XRD), single crystal X-ray crystallography, and infrared spectrometry among other techniques.

SUMMARY OF INVENTION

The invention relates to crystalline 1H-Imidazo[4,5-b]pyridin-5-amine, 7-[5-[(cyclohexylmethylamino)-methyl]-1H-indol-2-yl]-2-methyl, sulfate (1:1), trihydrate, E6070, its preparation, and its therapeutic uses. Accordingly, a pharmaceutical composition comprising crystalline E6070 and a pharmaceutically acceptable carrier represents one embodiment of the invention. The invention also relates to methods for treating an inflammatory disorder, an autoimmune disorder, or a proliferative disorder comprising the step of administering to a patient in need thereof a therapeutically effective amount of crystalline E6070. The crystalline E6070 may be administered neat or as a pharmaceutical composition of the invention.

DETAILED DESCRIPTION OF THE INVENTION

Figure 1:
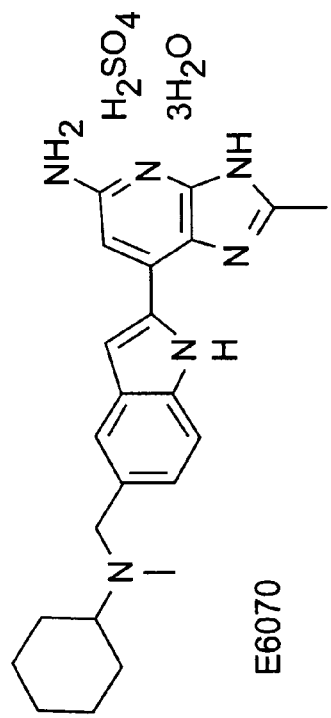
FIG. 1 shows a preferred preparation of crystalline E6070.
Figure 1:
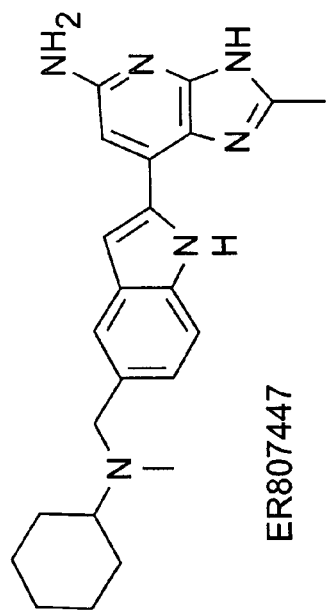

E6070, 1H-imidazo[4,5-b]pyridin-5-amine, 7-[5-[(cyclohexylmethylamino)-methyl]-1H-indol-2-yl]-2-methyl, sulfate (1:1), trihydrate, is the tri-hydrated, sulfuric acid salt of ER-807447. E6070 has the chemical structure (I) and the molecular formula: $C_{23}H_{36}N_6O_7S$ (CAS Registry Number: 532391-43-8).

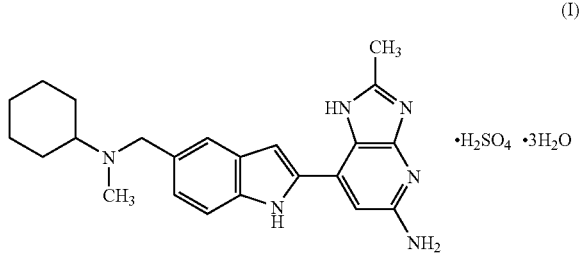

(I)

Possessing the same ability to inhibit NF-κB activation through inhibition of the IKKβ protein kinase as ER-807447, E6070 is useful as a therapeutic agent for the treatment of rheumatoid arthritis as well as other inflammatory or autoimmune and proliferative diseases and disorders. E6070 can be used for the treatment of diseases and disorders including, but not limited to, rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer. This invention relates to crystalline E6070 and its use as a therapeutic agent to treat such diseases and disorders.

Preparation of Crystalline E6070

The invention also relates to method for the preparation of crystalline E6070, according to the following reaction:

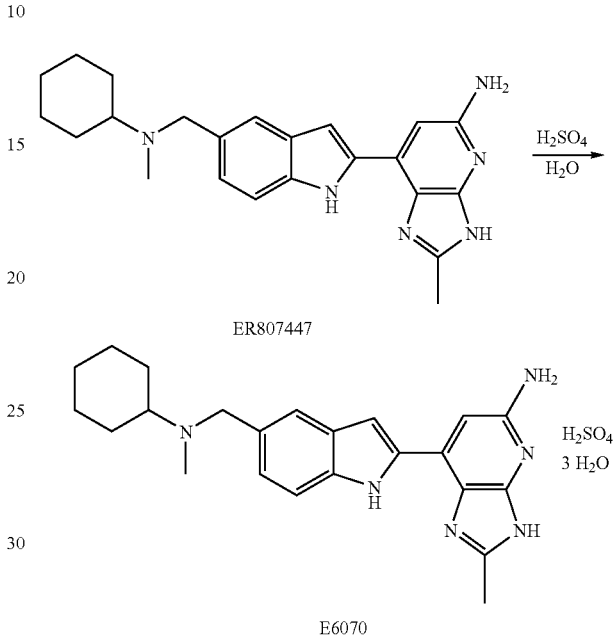

According to the method, ER807447 is first suspended in water to form an aqueous suspension. Sulfuric acid is added to the aqueous suspension to form a solution while keeping the internal temperature of the solution below 25° C. The solution typically has a yellow color. The solution may optionally be filtered to remove particulates from the solution. Other techniques for removing particulates known in the art, centrifuging, etc. may be used as the filtering step. The solution is then slowly warmed until E6070 crystallizes from solution. The solution may be warmed to about 100° C. Typically crystal formation occurs at temperatures of about 70° C. Preferred rates of warming typically range from about 30 minutes to 5 hours. Longer or shorter times may be used, particularly depending upon the batch size. E6070 may not crystallize as readily from highly dilute solutions.

To enhance crystallization, an anti-solvent may be used in the method of making the crystalline E6070 or to recrystallize crystalline E6070. The recrystallization procedure is described in Example 5. In the above method, the anti-solvent may be added to the aqueous suspension before sulfuric acid addition or to the solution after sulfuric acid addition and the optional filtration step. Useable anti-solvents and their use are known in the art. Typical anti-solvents include water-miscible anti-solvents such as, for example, methanol, ethanol, 1-propanol, 2-propanol, acetone and mixtures thereof. When an anti-solvent is used, the solution may become cloudy. It is generally not necessary to warm the solution to as high of temperatures as when just using an aqueous solution.

Crystalline E6070 may be prepared by forming the sulfuric acid salt of ER807747 according to the following procedure: Suspend ER807447 (1 wt) in water (10 vols) and stir. Add 1 M $H_2SO_4$ (1 eq., 2.6 vols) keeping the internal temperature below 25° C. A yellow solution forms immediately. Filter the solution and transfer the filtrate to a reactor with water (10 vols). Add seed crystal (0.01 wt). Warm slowly to 70° C. over 2.5 h. As the temperature increases, E6070 begins to crystallize from solution. Stir at 70° C. for 30 min then cool slowly to RT over 2 h. Filter over paper (P5) and wash with water (2×10 vol). Dry under $N_2$/vacuum to provide E6070 as a yellow free flowing crystalline powder (1.2 wts, 91%).

Process Parameters

Max scale: 5.9 kg

Min stir volume: 10 vols

Max stir volume: 20 vols

Yield: 91%, 99.95% HPLC purity

Crystalline E6070

In its crystalline form, E6070 is a yellow to orange-yellow or peach solid depending on the particle size. The smaller the particle size the more yellow the crystalline E6070 appears. At larger particles sizes, crystalline E6070 has an orange-yellow or peach color. Milling larger crystalline E6070 particles results in smaller particles with a yellow color but no change in the crystalline form of E6070.

The water content of crystalline E6070 is about 10%, identifying E6070 as a tri-hydrate form of the sulfuric acid salt of ER-807447. As discussed in the preparation of crystalline E6070 above, the crystalline product begins to precipitate as the solution is heated. Crystal precipitation from a warming solution is both remarkable and unusual. In contrast to the limited solubility of crystalline E6070, amorphous E6070 is very soluble in water, more than 10-times more soluble than crystalline E6070. Crystalline E6070, with its three waters of hydration, is much less soluble in water and also has very low hygroscopicity. These properties cause crystalline E6070 to be more stable than its amorphous form. Crystalline E6070 may be prepared from its amorphous form by dissolving the amorphous form in water and gradually heating the solution to precipitate crystalline E6070 or by adding an anti-solvent to the aqueous E6070 solution.

Crystalline E6070 may also be prepared from a variety of solvent systems. As described in Example 4 nineteen lots of E6070 were recrystallized from various solvent systems. For the seventeen lots analyzed, all showed the same crystal form. Additionally, there were no significant differences in water content and sulfuric acid ion content among the seventeen lots analyzed.

As described below in the Examples and shown in the Figures, crystalline E6070 was characterized by infrared (IR) spectroscopy, X-ray powder diffraction (XRD), single crystal X-ray diffraction, thermal analyses, hygroscopicity measurements, and solid state $^{13}$C NMR spectroscopy. The crystalline E6070 trihydrate is non-hygroscopic although it will dehydrate (lose all water) upon heating to 150° C. The variable temperature X-ray powder diffraction (XRD) patterns indicate that water loss results in reversible amorphism and as the dehydrated E6070 can return to its hydrate, stable crystalline state upon exposure to atmospheric moisture. See FIGS. 9 and 10.

Pharmaceutical Compositions

The invention relates to pharmaceutical compositions comprising a therapeutically effective amount of crystalline E6070 and a pharmaceutically acceptable carrier, (also known as a pharmaceutically acceptable excipient). As discussed above E6070 possesses biological properties making it useful for the treatment of inflammatory, autoimmune, and/or proliferative diseases and disorders. Pharmaceutical compositions for the treatment of those diseases and disorders contain a therapeutically effective amount of crystalline E6070 as appropriate for treatment of a patient with the particular disease or disorder.

A "therapeutically effective amount" of crystalline E6070 (discussed here concerning the pharmaceutical compositions and below concerning the methods of treatment according to the invention) refers to an amount sufficient to reduce the effects of an inflammatory or autoimmune response or disorder or sufficient to prevent, kill, or inhibit the growth of tumor cells. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; and the rate of excretion of E6070; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

A pharmaceutical composition of the invention may be any pharmaceutical form which maintains the crystalline form of E6070. The pharmaceutical composition may be a solid form, a liquid suspension, an injectable composition, a topical form, or a transdermal form. These forms are disclosed in published PCT application W2004/06336 A2 and published U.S. application 2004/0186127 A1, which are incorporated here by reference.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having crystalline E6070, a carrier should be chosen that maintains the crystalline E6070. In other words, the carrier should not substantially alter the crystalline form of E6070, for example, a liquid carrier which would dissolve the crystalline E6070 should not be used. Nor should the carrier be otherwise incompatible with E6070, such as by producing any undesirable biological effect or otherwise interacting in a deleterious manner with any other component(s) of the pharmaceutical composition.

The pharmaceutical compositions of the invention are preferably formulated in unit dosage form for ease of administration and uniformity of dosage. A "unit dosage form" refers to a physically discrete unit of therapeutic agent appropriate for the patient to be treated. It will be understood, however, that the total daily dosage of E6070 and its pharmaceutical compositions according to the invention will be decided by the attending physician within the scope of sound medical judgment.

Because the crystalline form of E6070 is more easily maintained during their preparation, solid dosage forms are a preferred form for the pharmaceutical composition of the invention. Solid dosage forms for oral administration, which include capsules, tablets, pills, powders, and granules, are particularly preferred. In such solid dosage forms, the active compound is mixed with at least one inert, pharmaceutically acceptable carrier such as sodium citrate or dicalcium phosphate. The solid dosage form may also include one or more of: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate. The solid dosage forms may also comprise buffering agents. They may optionally contain opacifying agents and can also be of a composition that they release the active ingredient(s) only, or preferentially, in a certain part of the intestinal tract, optionally, in a delayed manner Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions of the invention can also be prepared with coatings and shells such as enteric coatings and other coatings well known in the pharmaceutical formulating art.

Crystalline E6070 can be in a solid micro-encapsulated form with one or more carriers as discussed above. Microencapsulated forms of crystalline E6070 may also be used in soft and hard-filled gelatin capsules with excipients such as lactose or milk sugar as well as high molecular weight polyethylene glycols and the like.

Preferred solid pharmaceutical compositions of the invention are 7 mm-diameter, round, bi-convex yellow film-coated tablets containing 1, 10, or 50 mg of crystalline E6070 as the active pharmaceutical ingredient. All strengths are manufactured through a wet granulation process. The carriers (or excipients) in these preferred pharmaceutical compositions include: Mannitol, Starch, Crospovidone, Povidone, Magnesium stearate, Hydroxypropylmethylcellulose 2910, Talc, Polyethylene glycol 8000, Titanium dioxide, and Ferric oxide (Yellow).

Methods of Treatment Using Crystalline E6070

The invention also provides methods for the treatment of inflammatory or autoimmune disorders and the treatment of proliferative disorders. Without wishing to be bound by any particular theory and as discussed above, E6070 inhibits adhesion molecule expression such as E-selectin and ICAM-1 on the endothelial cell surface induced by stimulation with inflammatory cytokines. Such cell surface molecules play a critical role for inflammatory cell infiltration and cell-cell interactions within inflammatory and immune responses. E6070 also reduces activation of the transcriptional factor NF-κB and inhibit the transcriptional activation in inflammatory cytokine signaling pathways, which regulates many genes such as IL-1 and TNF involved in the pathology of several inflammatory diseases. More generally, the identification of NF-κB as a key player in the pathogenesis of inflammation suggest that NF-κB targeted therapeutics may be effective in inflammatory and immune disorders (see, generally, NF-κB in Defense and Disease, *J. Clin. Investig.* 2001, 107, 7).

To treat inflammatory, autoimmune or proliferative diseases and disorders, crystalline E6070 and pharmaceutical compositions containing it may, according to the invention, be administered using any amount, any form of pharmaceutical composition and any route of administration effective for the treatment. In other words, after formulation with an appropriate pharmaceutically acceptable carrier in a desired dosage, appropriate pharmaceutical compositions containing crystalline E6070 may be administered to a patient orally, rectally, parenterally, intracisternally, intravaginally, intraperitoneally, topically (as by powders, ointments, or drops), bucally, as an oral or nasal spray, or the like.

In the methods of the invention, crystalline E6070 is administered in a therapeutically effective amount. Typically, crystalline E6070 may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. Dosages smaller than 0.001 mg/kg or greater than 50 mg/kg (for example 50-100 mg/kg) may also be administered to a patient undergoing treatment.

Preparation and Characterization of Crystalline E6070

EXAMPLE 1

Preparation of Crystalline E6070

Crystalline E6070 was synthesized using the process described above and shown in FIG. 1. The solvents used were special grade. All other chemicals were of analytical grade. Elemental Analysis: The carbon, hydrogen, nitrogen, and sulfur contents of E6070 were determined by Quantitative Technologies, Inc. (QTI), Whitehouse N.J., USA. C, H, and N were determined by combustion analysis using a 2400 Perkin-Elmer CHN Elemental Analyzer. Sulfur content was determined by combustion analysis, followed by a barium perchlorate titration. The percent elemental composition values for C, H, N, and S, as determined by QTI, is in agreement with the molecular formula $C_{23}H_{36}N_6O_7S$ of E6070. The experimental values were all within ±0.3% of the theoretical value. The theoretical and experimental values both account for the drug molecule plus one sulfuric acid molecule and three water molecules.

TABLE 1

Results of Elemental Analysis

|  | C | H | N | S |
|---|---|---|---|---|
| Theory: | 51.10 | 6.71 | 15.54 | 5.93 |
| Found: | 51.11 | 6.57 | 15.42 | 5.99 |

EXAMPLE 2

Infrared Spectrum of Crystalline E6070

Figure 2:
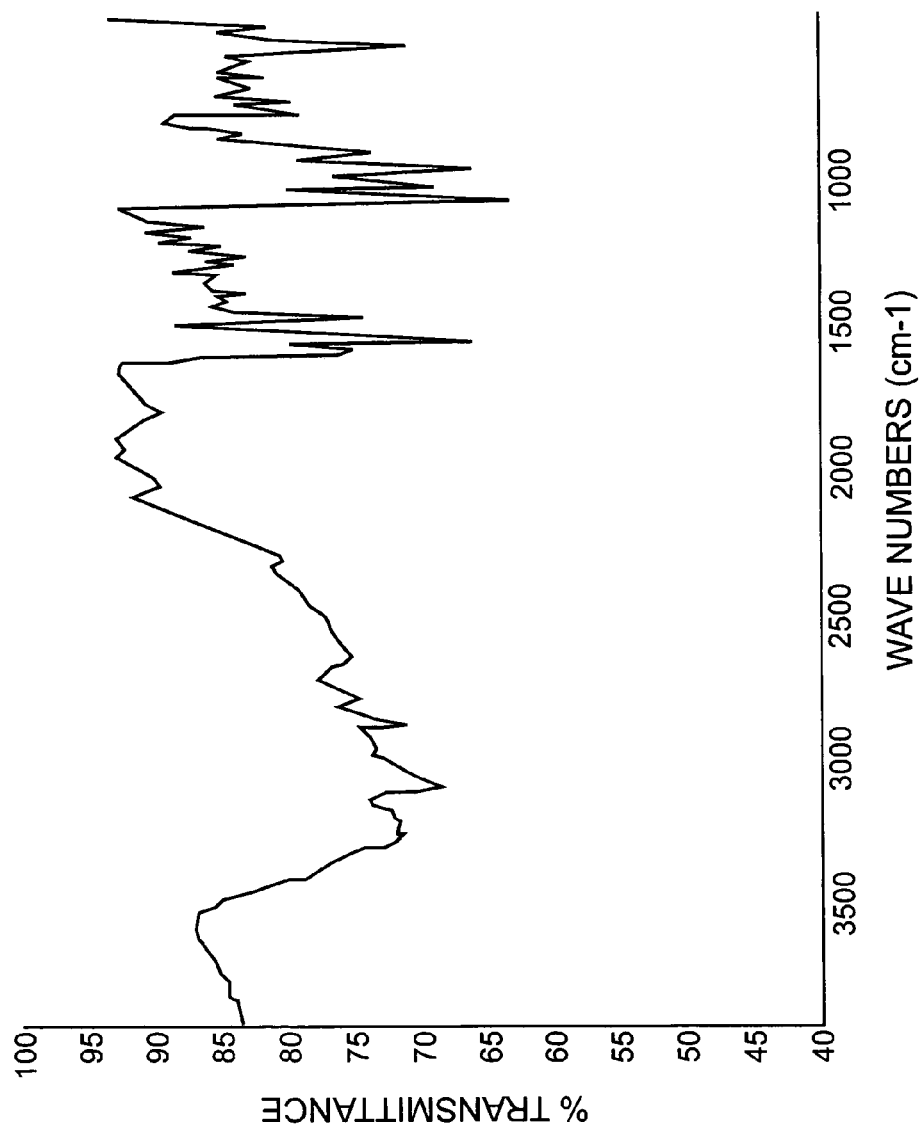
FIG. 2 is an infrared spectrum of crystalline E6070.

The IR absorption spectrum of E6070 was recorded for a neat powder run on a Nicolet Magna-IR 550 Fourier Transform Infrared Spectrometer with a DuraSampl/R II Diamond-ATR sampling accessory (SensIR Technologies, Danbury Conn.). The IR absorption spectrum of crystalline E6070 is shown in FIG. 2. The assignment of the characteristic absorption bands of was consistent with the assigned structure of crystalline E6070 as shown in Table 2. Preferably, crystalline E6070 is characterized by having at least two absorption bands in an infrared spectrum of a neat sample selected from 1656, 1620, 1549, 1136, 1085, and 1033 cm$^{-1}$.

TABLE 2

Characteristic Absorption Bands of Crystalline E6070

| Wavenumber (cm$^{-1}$) | Intensity | Assignment |
|---|---|---|
| 3400–3200 | Strong | ν N—H |
| 3200–2800 | Strong | ν C—H |
| 2705 | Medium | ν N—H (ammonium salt) |
| 1656 | Medium | δ N—H |
| 1620, 1549 | strong | ν C═N, ν C═C |
| 1136, 1085 | strong | ν S═0, δ C—H |
| 1033 | strong | δ C—H |

ν: stretching vibration,
δ: bending vibration

EXAMPLE 3

Powder X-ray Diffraction Pattern of Crystalline E6070

Figure 3:
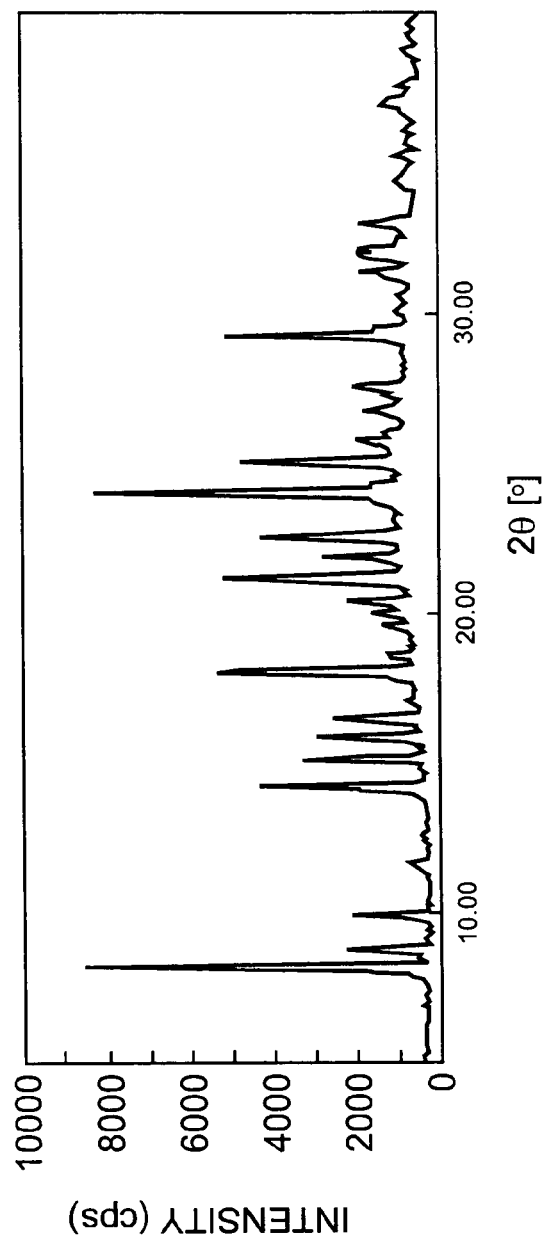
FIG. 3 depicts a powder X-ray diffraction pattern of crystalline E6070.

Crystalline E6070 was placed on the sample platform of an X-ray powder diffractometer (RINT-2000, Rigaku, Japan) and analyzed under the conditions shown in Table 3. FIG. 3 shows the powder X-ray diffraction (XRD) pattern for crystalline E6070.

TABLE 3

Powder X-ray Diffraction Measurement Conditions

Target: Cu
Detector: Scintillation counter
Tube voltage: 40 kV
Tube current: 200 mA
Slit: DS ½°, RS 0.3 mm, SS ½°
Scan speed: 2°/min
Step/Sampling: 0.02°
Scan range: 5 to 40°
Sample holder: Glass holder (diameter: 5 mm)
Goniometer: Vertical goniometer
Monochromater: used

EXAMPLE 4

Single Crystal X-ray Diffraction Analysis and Calculated XRD Pattern of Crystalline E6070

Approximately 1.8 mg of E6070 was weighed using an AT250 balance (Mettler, Switzerland) and dissolved in 3.0 mL of a mixture of acetone (1.5 mL) and water (1.5 mL) with heating. This solution was stored at room temperature in a desiccator. After storing this solution for three days, small prismatic crystals appeared.

A crystal of the E6070 with approximate dimensions of 0.10×0.10×0.05 mm was mounted on a glass fiber. Diffraction data was collected on a R-AXIS V imaging plate detector system (Rigaku, Japan) with ω axis oscillation method (oscillation range: −100° to 100°; step: 10°) using a wavelength of 0.75 Å. All measurements were performed on Pharmaceutical Industry Beamline BL32B2 at SPring-8 (Super Photon ring-8 GeV). The collected data were processed using CrystalClear for structural analysis.

The crystal structure was solved with the final R factor 0.072. The results of the data collection and crystallographic analysis of the E6070 crystal are summarized in Table 4.

TABLE 4

Data Collection and Crystallographic Analysis of Single Crystal E6070

| Crystal Data | |
|---|---|
| Crystal System | monoclinic |
| Space Group | P2$_1$/n |
| Lattice Parameters | a = 16.915(3) Å |
| | b = 12.384(2) Å |
| | c = 12.554(2) Å |
| | β = 97.089(8)° |
| | V = 2609.7(9) Å$^3$ |
| Z value | 4 |
| Data Collection | |
| Diffractometer | R-AXIS V |
| Radiation | Synchrotron radiation |
| | γ = 0.75 Å |
| No. of Reflections Measured | Total: 20149 |
| | Unique: 5642 |
| R$_{merge}$ (16.79–0.73 Å) | 3.3% |
| Completeness (16.79–0.73 Å) | 79.9% |
| Structure Solution and Refinement | |
| Structure Solution | Direct Methods |
| | (SHELXS-97) |
| Refinement | Full-matrix least-squares |
| | (SHELXL-97) |
| No. Reflections | 4630 |
| No. Variables | 470 |
| Reflection/Parameter Ratio | 9.85 |
| Residuals: R; Rw*. | 0.072; 0.207 |

*R: unweighted R factor, Rw: weighted R factor

Figure 4:
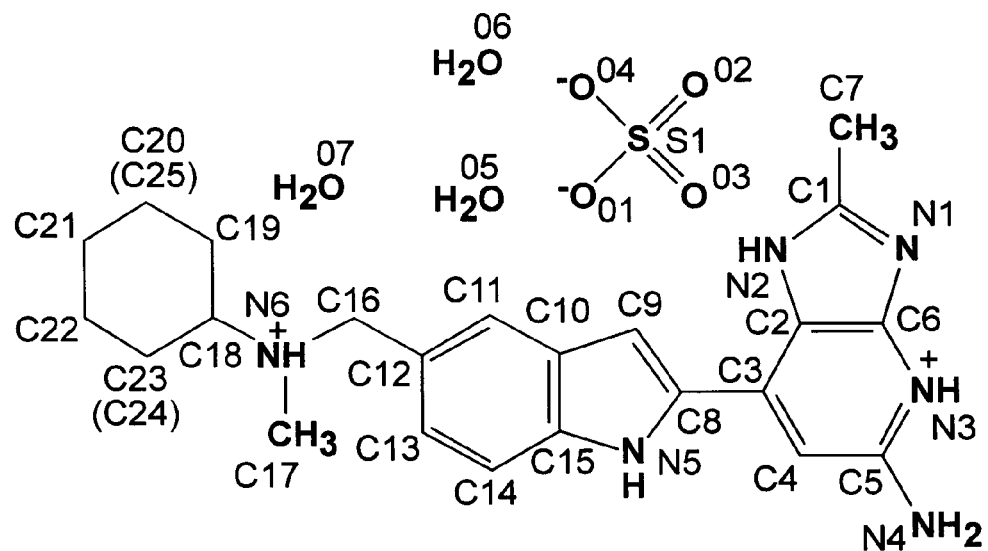
FIG. 4 is the numbering diagram of the E6070 single crystal analysis.
Figure 4:
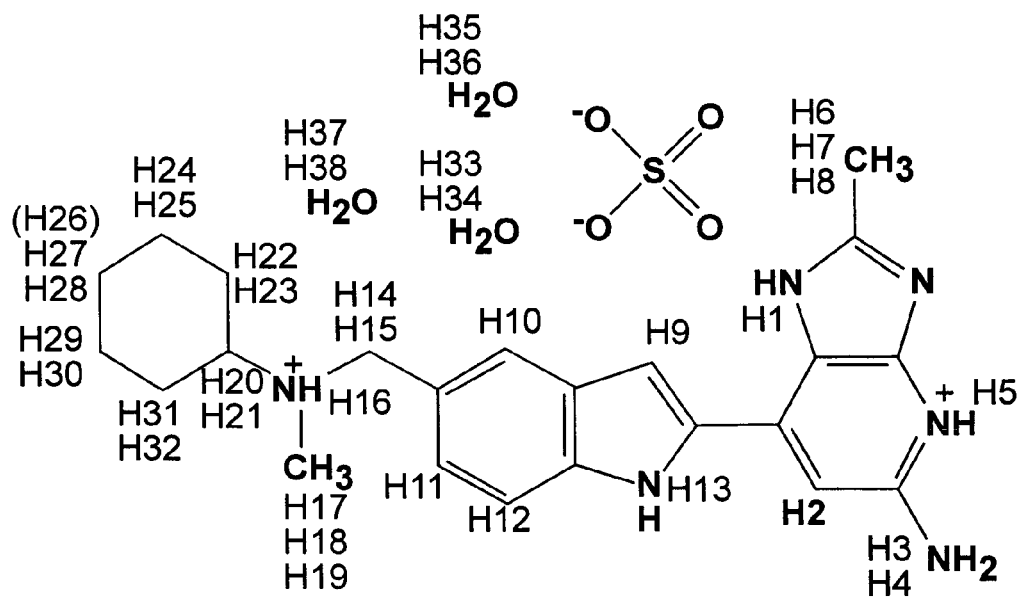
Figure 5:
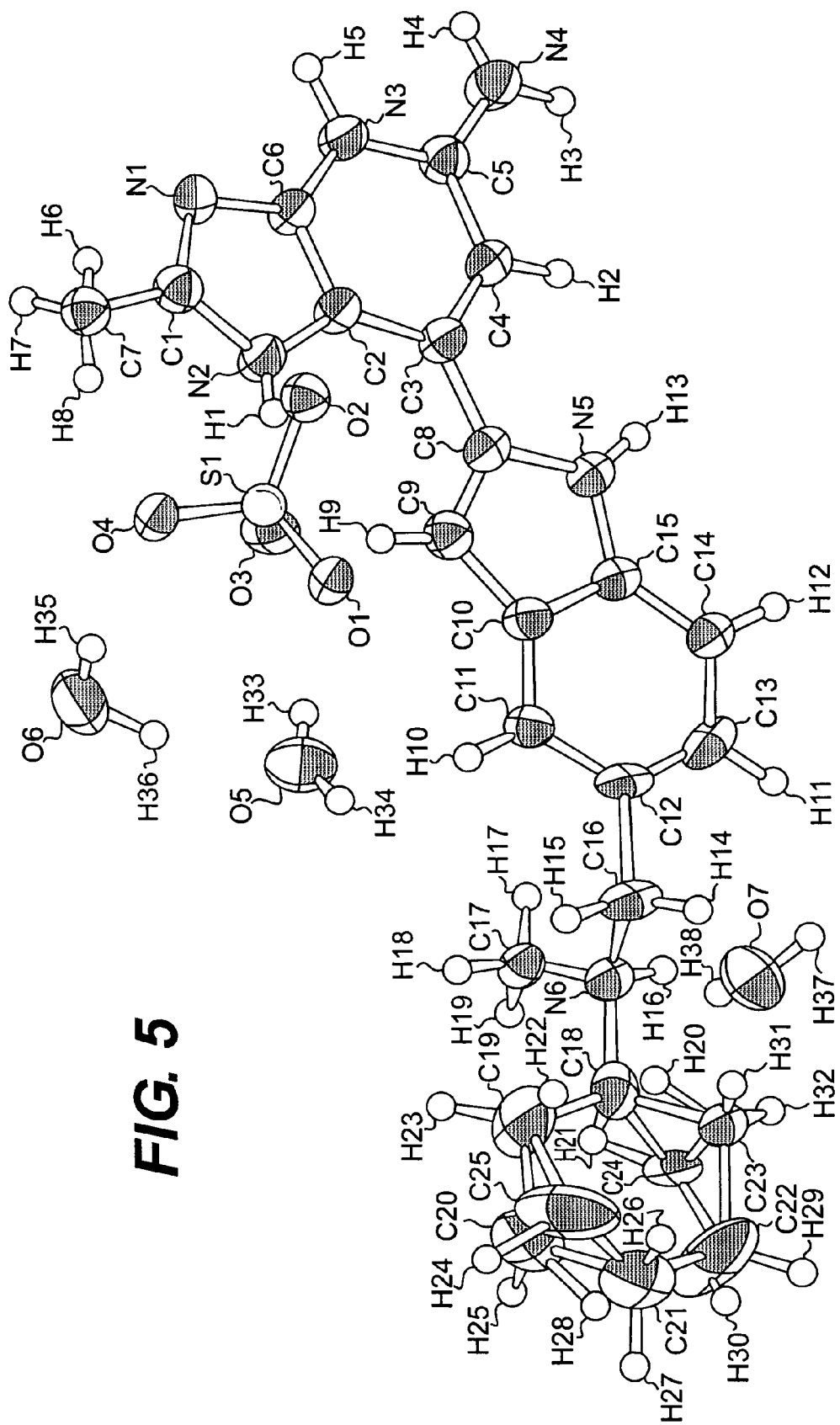
FIG. 5 is ORTEP drawing of the E6070 crystal for its asymmetric unit.

The numbering diagram of X-ray crystallographic analysis and the ORTEP drawing are shown in FIGS. 4 and 5, respectively. In FIG. 5, the thermal ellipsoids are shown at the 50% probability levels.

Figure 6:
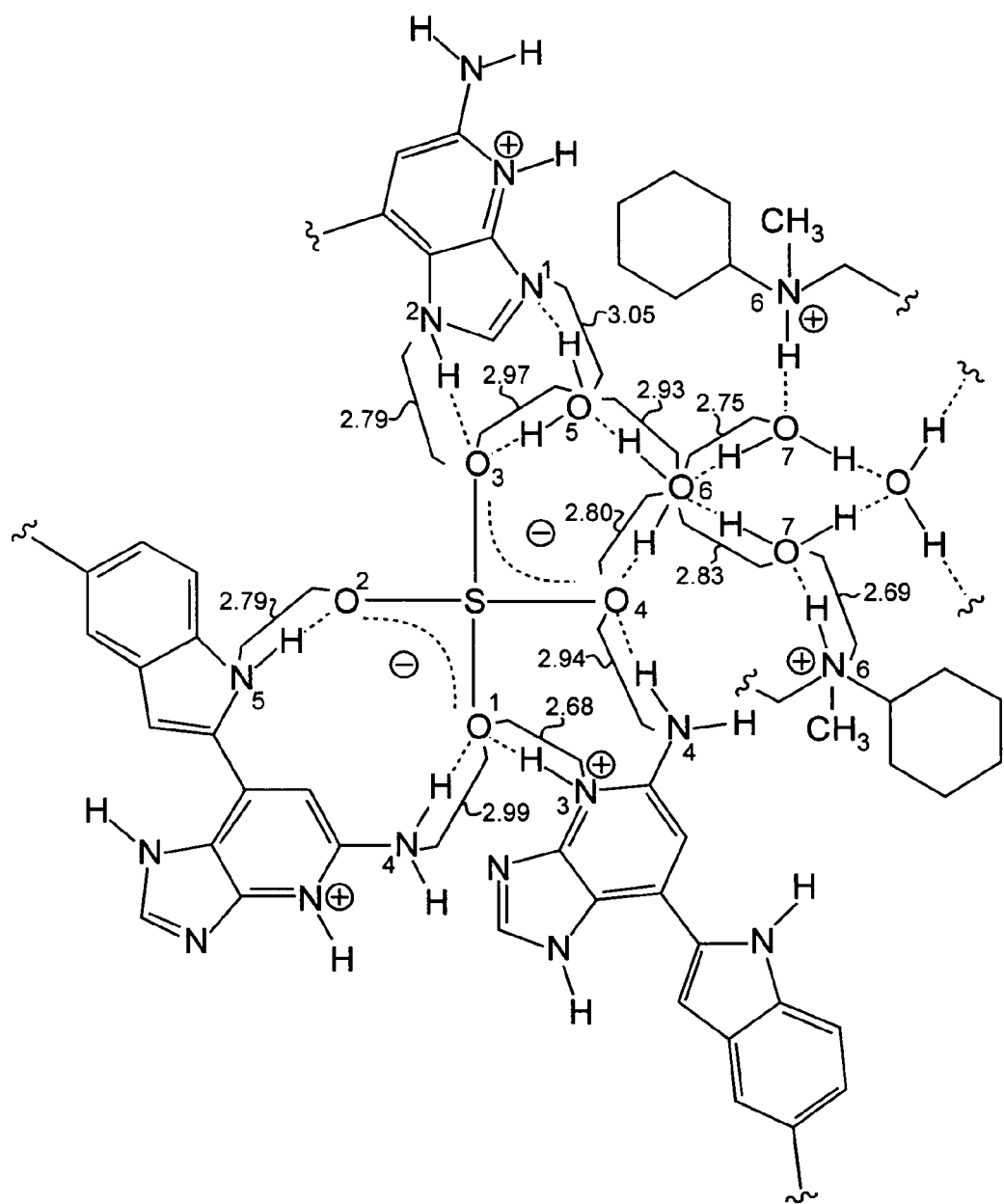
FIG. 6 depicts the hydrogen bond network of crystalline E6070 and its intermolecular contacts.

The crystal structure showed the protonated N-methylamine (N6) and imidazopyridine ring (N3) of the active ingredient, one SO$_4^{2-}$ Ion, and Three Water Molecules in The asymmetric unit. E6070 formed the H$_2$SO$_4$ salt by a hydrogen-bond network through water molecules as shown in FIG. 6. In the ORTEP drawing, (FIG. 5), the disorder of two carbon atoms of the cyclohexane ring was observed. This behavior may be due to the conformational change in that part. Based on the above, the structure of E6070 was determined as presented above in FIG. 5.

Figure 7:
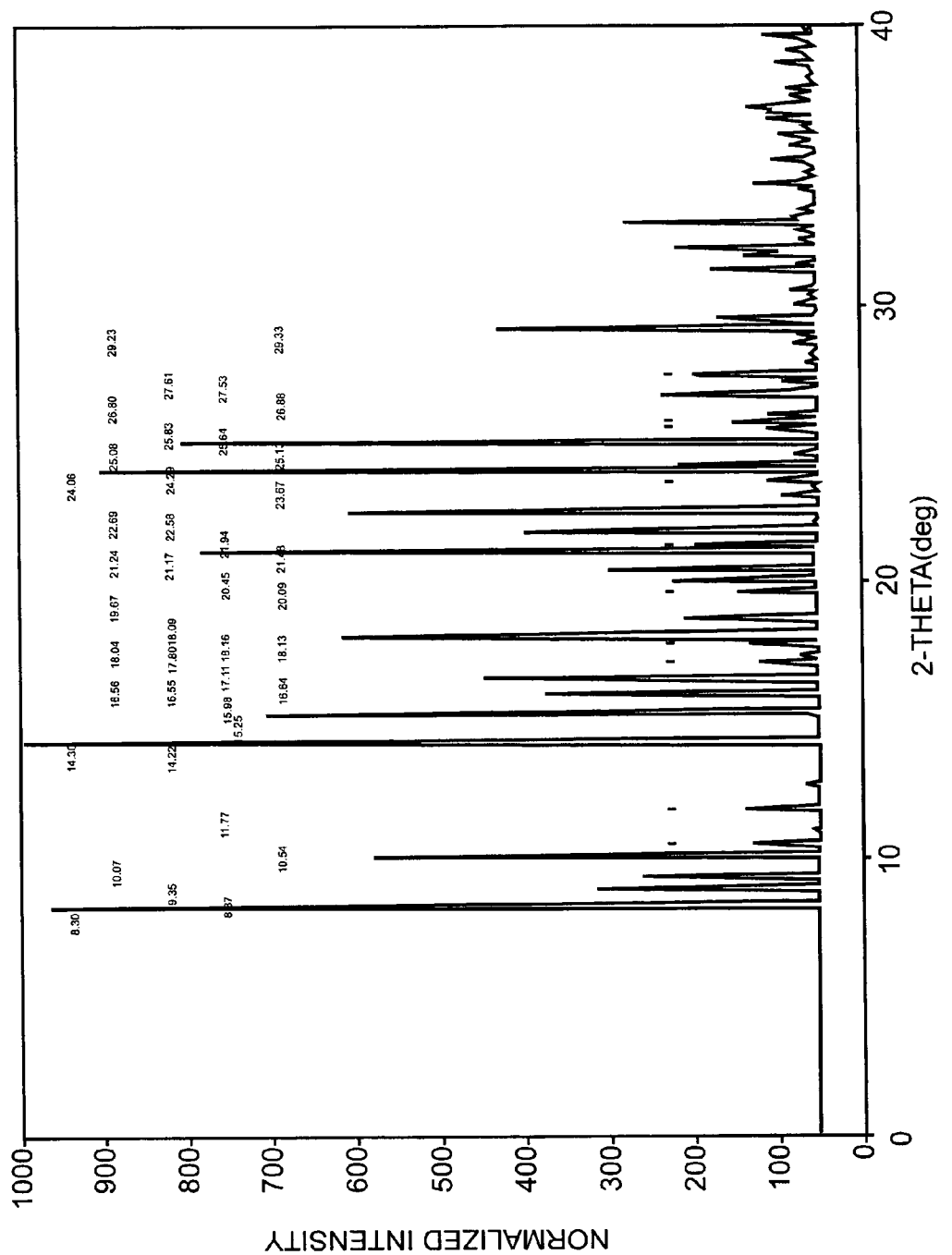
FIG. 7 depicts the X-ray diffraction pattern as calculated from the single crystal data of E6070.

FIG. 7 depicts the X-ray powder diffraction data calculated from the single crystal data. The calculated powder diffraction pattern matches the XRD patterns for crystalline E6070 (compare, for example, FIG. 3). This shows that the single crystal of E6070 is isomorphous with the E6070 crystalline powder.

EXAMPLE 5

Effect of Crystallization from Various Solvents

Figure 8:
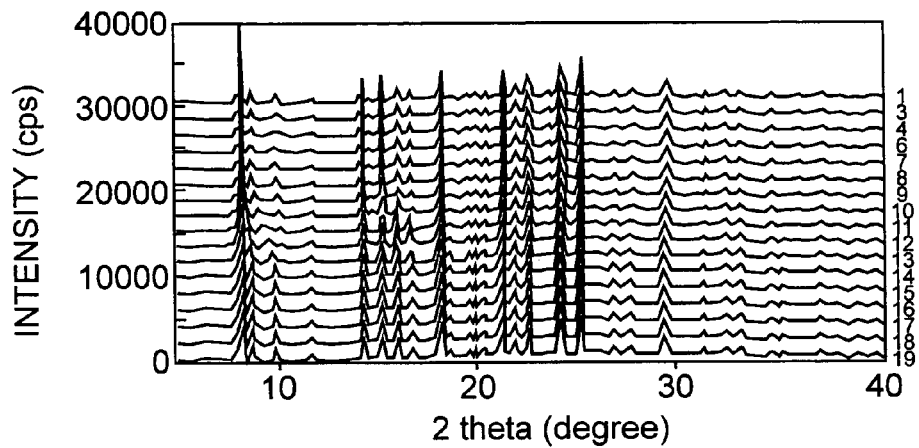
FIG. 8 depicts XRD patterns for 17 lots of crystalline E6070 recrystallization from various solvent systems.

E6070 was crystallized on about one hundred mg scale from 19 solvent systems as shown in Table 5 because the nature of the crystallizing solvent is a known factor in the isolation of various polymorphs of organic compounds. Recrystallized E6070 was prepared by dissolving the sample in water followed by the addition of suitable anti-solvents. Table 5 below lists the anti-solvents used. Where no anti-solvent is indicated, the E6070 was recrystallized by warming the aqueous solution to 100° C. before cooling to room temperature. As shown in FIG. 8, no significant differences were observed in the XRD patterns of the crystallized materials except for only two lots, i.e. (lot 2) and (lot 5), which showed lower XRD intensity than the other lots (data not shown). Also, all lots showed almost the same water content and sulfuric acid ion content (Table 6). These results indicated that E6070 exists in a stable crystalline form.

TABLE 5

Crystallization Solvents

| Lot No. | Solvent | E6070 concentration |
|---|---|---|
| 1 | ethanol/water (1:4.5, v/v) | about 13 mg/mL |
| 2 | Water | about 500 mg/1.3 mL |
| 3 | Water | about 50 mg/1.1 mL |
| 4 | acetone/water (1.3:1, v/v) | about 19 mg/mL |
| 5 | 1-propanol/water (1.5:1, v/v) | about 17 mg/mL |
| 6 | 2-propanol/water (1.8:1, v/v) | about 16 mg/mL |
| 7 | Water | about 389 mg/mL |
| 8 | acetone/water/EtOH (2:1:1.7, v/v/v) | about 16 mg/mL |
| 9 | ethanol/water (1:2.2, v/v) | about 21 mg/mL |
| 10 | Water | about 13 mg/mL |
| 11 | acetone/water (1:2, v/v) | about 29 mg/mL |
| 12 | acetone/water (1:4, v/v) | about 37 mg/mL |
| 13 | acetone/water (1:3, v/v) | about 34 mg/mL |
| 14 | Water | about 36 mg/mL |
| 15 | Water | about 17 mg/mL |
| 16 | 2-propanol/water (1:1, v/v) | about 23 mg/mL |
| 17 | Water | about 73 mg/mL |
| 18 | ethanol/water (1:1.6, v/v) | about 61 mg/mL |
| 19 | ethanol/water (5:1, v/v) | about 65 mg/mL |

TABLE 6

Water and Sulfuric Acid Ion Content of E6070

| Lot No. | Water Content* (%) | $SO_4^{2-}$ Content* (%) |
|---|---|---|
| Theoretical value | 10.0 | 17.8 |
| 1 | 9.7 | 17.1 |
| 3 | 9.1 | 23.7 |
| 4 | 10.1 | 20.1 |
| 6 | 9.9 | 18.3 |
| 7 | 9.8 | 17.5 |
| 8 | 10.0 | 17.5 |
| 9 | 9.8 | 17.7 |
| 10 | 9.8 | 18.2 |
| 11 | 10.0 | 17.7 |
| 12 | 10.0 | 17.9 |
| 13 | 9.7 | 17.5 |
| 14 | N.T. | 17.5 |
| 15 | N.T. | 18.5 |
| 16 | N.T. | 18.1 |
| 17 | N.T. | 17.8 |
| 18 | N.T. | 18.5 |
| 19 | N.T. | 18.6 |

N.T.: Not Tested
*A small quantity of sample was used for the above measurements.

EXAMPLE 6

Variable Temperature Powder X-Ray Diffractometry

Figure 9:
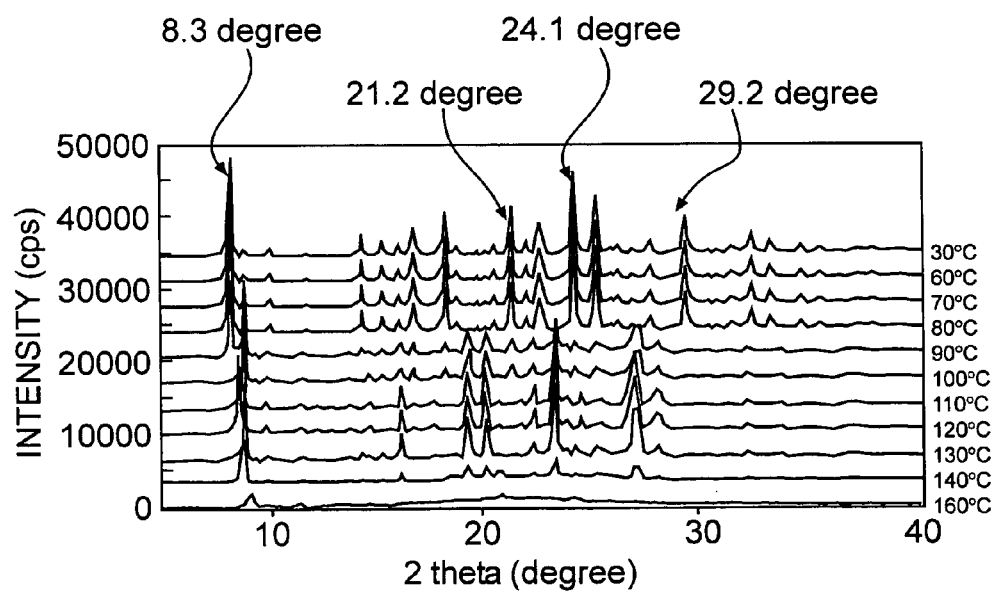
FIG. 9 depicts XRD patterns of crystalline E6070 at various temperatures.

Crystalline E6070 was packed into a sample holder and then placed on the platform of X-ray diffractometer, RINT-2000 (Rigaku, Japan). The XRD patterns of E6070 drug substance at various temperatures are shown in FIG. 9. The instrument was operated under the conditions listed in Table 7. Characteristic XRD peaks are identified in Table 8 and in FIG. 9. Peaks which may preferably be used to characterize and identify crystalline E6070 include 8.3±0.2° 2Θ, 10.1±0.2° 2Θ, 14.3±0.2° 2Θ, 15.3±0.2° 2Θ, 18.1±0.2° 2Θ, 21.1±0.2° 2Θ, 24.1±0.2° 2Θ, and 29.2±0.2° 2Θ. Any combination of these peaks would be useful in characterizing crystalline E6070. When the drug substance was heated in a stepwise manner from 30° C. to 160° C., a new diffraction pattern, which indicates a crystal transformation presumably due to water loss, was observed at 90° C. The peak intensities decreased gradually and completely disappeared above 160° C. Accordingly, loss of water in crystalline E6070 results both in crystal transformation and substantial lattice imperfection.

TABLE 7

Powder X-ray Diffraction Measurement Conditions

Target: Cu
Detector: Scintillation counter
Tube voltage: 40 kV
Tube current: 200 mA
Slit: DS ½°, RS 0.3 mm, SS ½°
Scan speed: 5°/min
Step/Sampling: 0.02°
Scan range: 5 to 40°
Sample holder: Glass or copper holder (diameter: 5 mm)
Goniometer: Vertical goniometer
Monochromater: used

TABLE 8

Characteristic X-ray powder diffraction (PXRD) peaks of E6070

| 2 theta (degree) |
|---|
| 8.3 ± 0.2 |
| 8.9 ± 0.2 |
| 10.1 ± 0.2 |
| 14.3 ± 0.2 |
| 15.3 ± 0.2 |
| 16.0 ± 0.2 |
| 16.6 ± 0.2 |
| 18.1 ± 0.2 |
| 20.5 ± 0.2 |
| 21.2 ± 0.2 |
| 22.6 ± 0.2 |
| 24.1 ± 0.2 |
| 25.1 ± 0.2 |
| 26.8 ± 0.2 |
| 27.6 ± 0.2 |
| 29.2 ± 0.2 |

Figure 10:
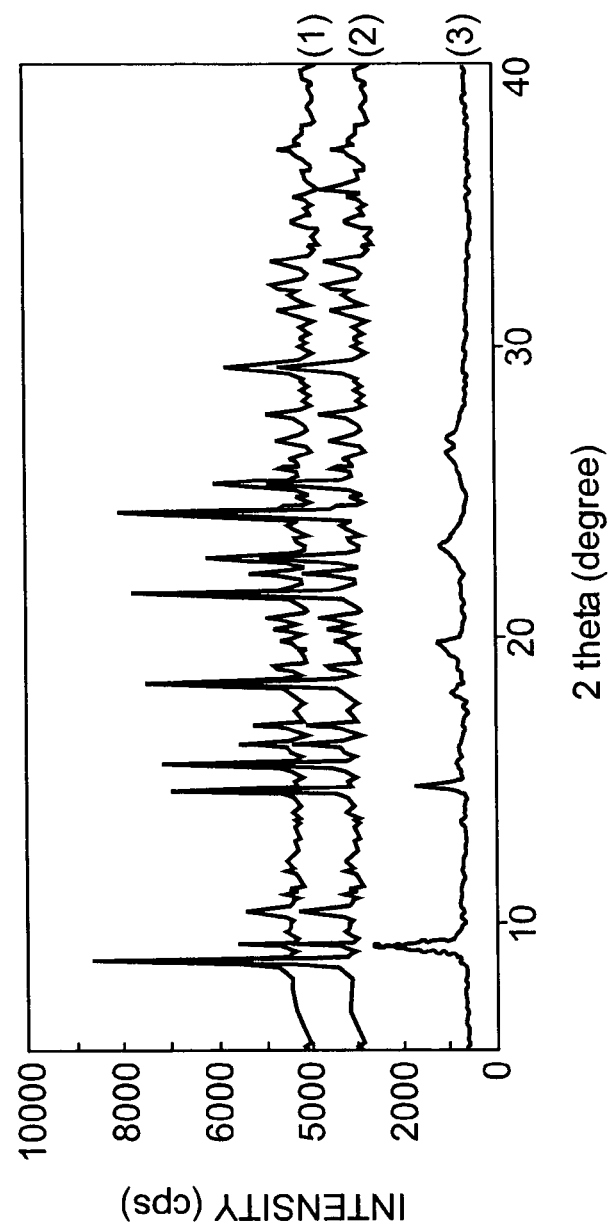
FIG. 10 depicts reversible XRD patterns for hydrated and dehydrated E6070.

As shown in FIG. 10, crystalline E6070 can undergo a reversible transition to its amorphous form. PXRD pattern (1) in FIG. 10 shows crystalline E6070 under ambient conditions (25° C., 60% relative humidity). Upon heating to 100° C., with concomitant loss of the waters of hydration, the PXRD pattern (3) shows a loss of crystallinity. Cooling back to ambient conditions rehydrates the E6070 and as shown in PXRD pattern (2) with a return of its crystalline form. This experiment was performed using the diffractomer described above.

EXAMPLE 7

Thermal and Hygroscopic Characterization of Crystalline E6070

Thermal Analyses: Using a Rigaku Thermoflex TAS20 TG8101D (Rigaku, Tokyo, Japan) therogravimetric-differential thermal analyses (TG-DTA) were performed under the measurement conditions in Table 9. The temperature axis and the cell constant were calibrated with indium. The solid sample (1-5 mg) was accurately weighed into an open aluminum pan and then heated.

TABLE 9

Thermal Analysis Measurement Conditions

Sample pan: aluminum pan
Reference: empty aluminum pan
Atmosphere: no purge condition
Heating rate: 10° C./min
Range of temperature: from 25° C. to 300° C.

Hygroscopicity Measurements: Samples were exposed to various relative humidity (RH) conditions at 25° C. using an automated controlled-atmosphere microbalance, MB-300W (VTI Corporation, FL, USA). In this system, a sample was suspended in an isothermal chamber at 25° C., and the RH was regulated from 5% to 95% by adjusting the relative flow rates of dry (0% RH) and moist (100% RH) nitrogen. The weight of the sample was measured every 2 min with the microbalance. The weight stability criterion employed for the equilibrium was that the maximum weight change for each measurement was less than 0.2% (w/w).

Figure 11:
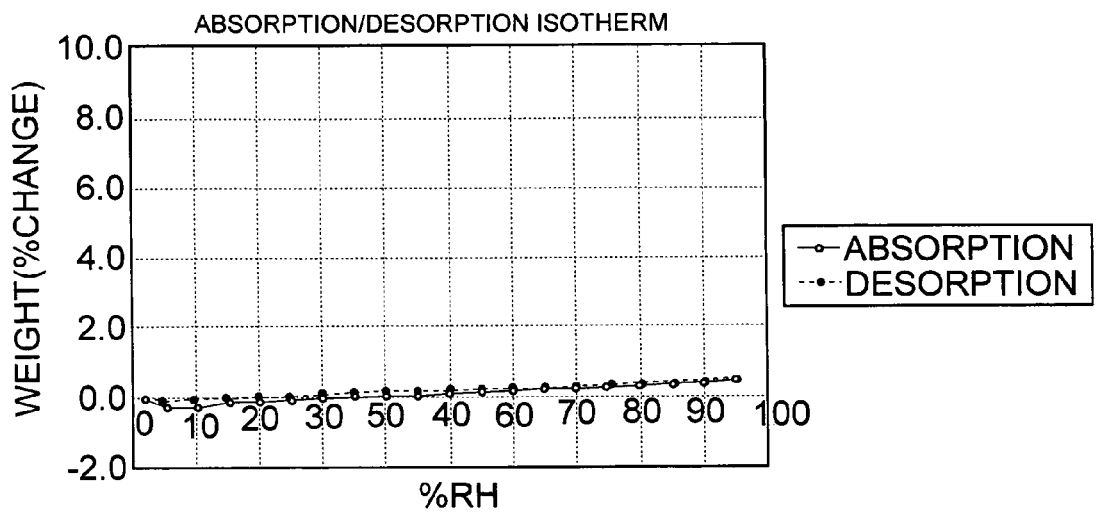
FIG. 11 depicts an adsorption/desorption isotherm for crystalline E6070.
Figure 12:
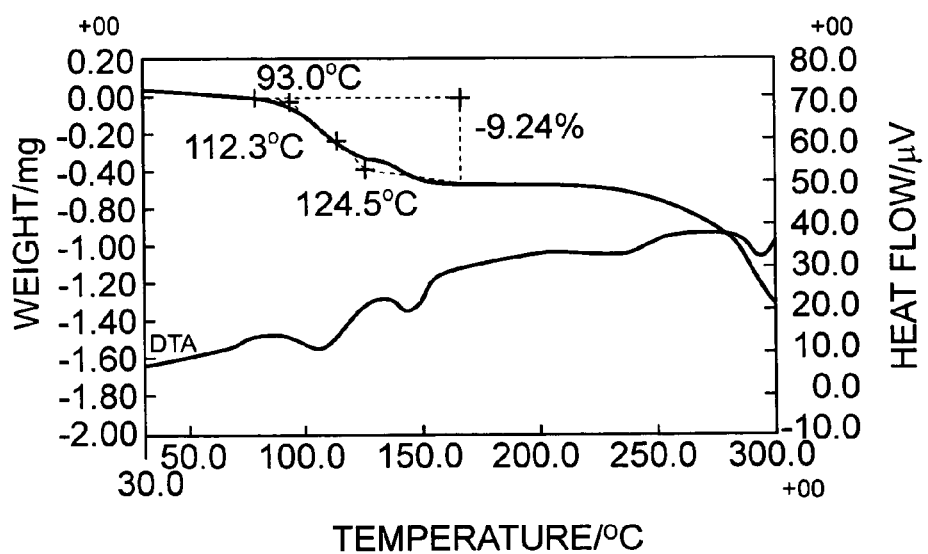
FIG. 12 depicts TG-DTA thermogram of crystalline E6070 in an open pan at the heating rate of 10° C./min.

Although crystalline E6070 includes about 10% of water, which is nearly equal to the water content of a trihydrate, it was not found to take up or lose any moisture of water when it was exposed to various controlled humidities, from 0% to 93% RH at 25° C. The absorption/desorption isotherm for this test is shown in FIG. 11. In the TG-DTA thermogram, about 10% of weight loss was observed in the temperature range from 90° C. to 150° C., where the DTA curve showed two broad endothermic peaks (FIG. 12). These endothermic peaks imply dehydration behavior of E6070 because the weight loss was comparable to its water content.

EXAMPLE 8

Physical Stability of Crystalline E6070

Figure 13:
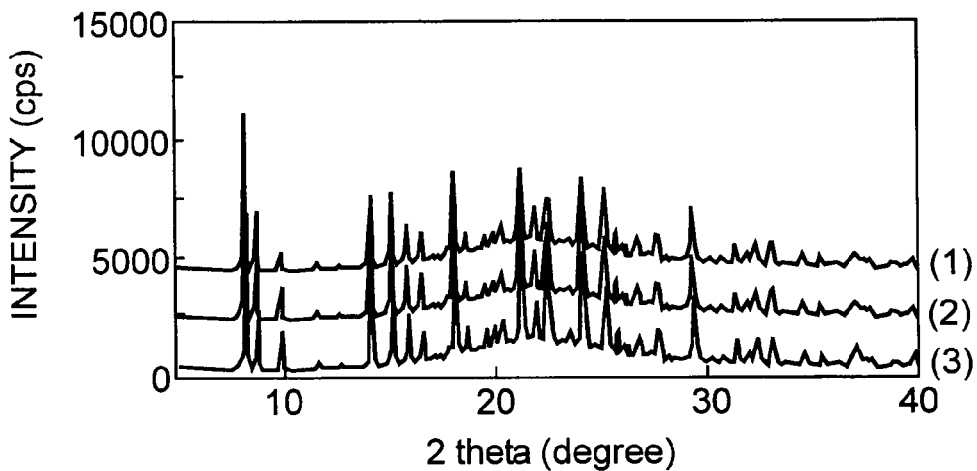
FIG. 13 depicts XRD Patterns for crystalline E6070: (1) initial, (2) 40° C./75% RH (1M), and (3) 60° C. (1M).
Figure 14:
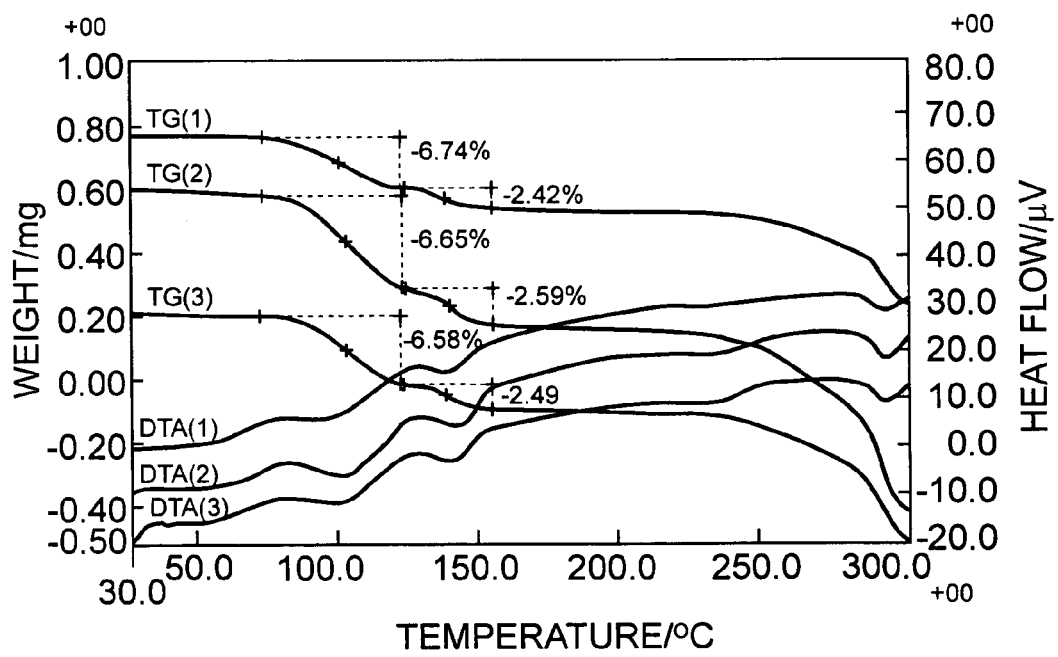
FIG. 14 depicts TG-DTA thermograms of crystalline E6070: (1) initial, (2) 40° C./75% RH (1M), and (3) 60° C. (1M).

The physical stability of crystalline E6070 was evaluated under the following two conditions: 60° C. for a month and 40° C./75% RH (open) for a month. As a result, no change was observed in XRD pattern under either stressed conditions (FIG. 13). Also, both stressed samples showed the same TG-DTA thermogram as the initial (FIG. 14). Therefore, crystalline E6070 was shown to be physically stable in the solid state.

EXAMPLE 9

Crystallization of E6070—1 g-Scale Batch

Figure 15:
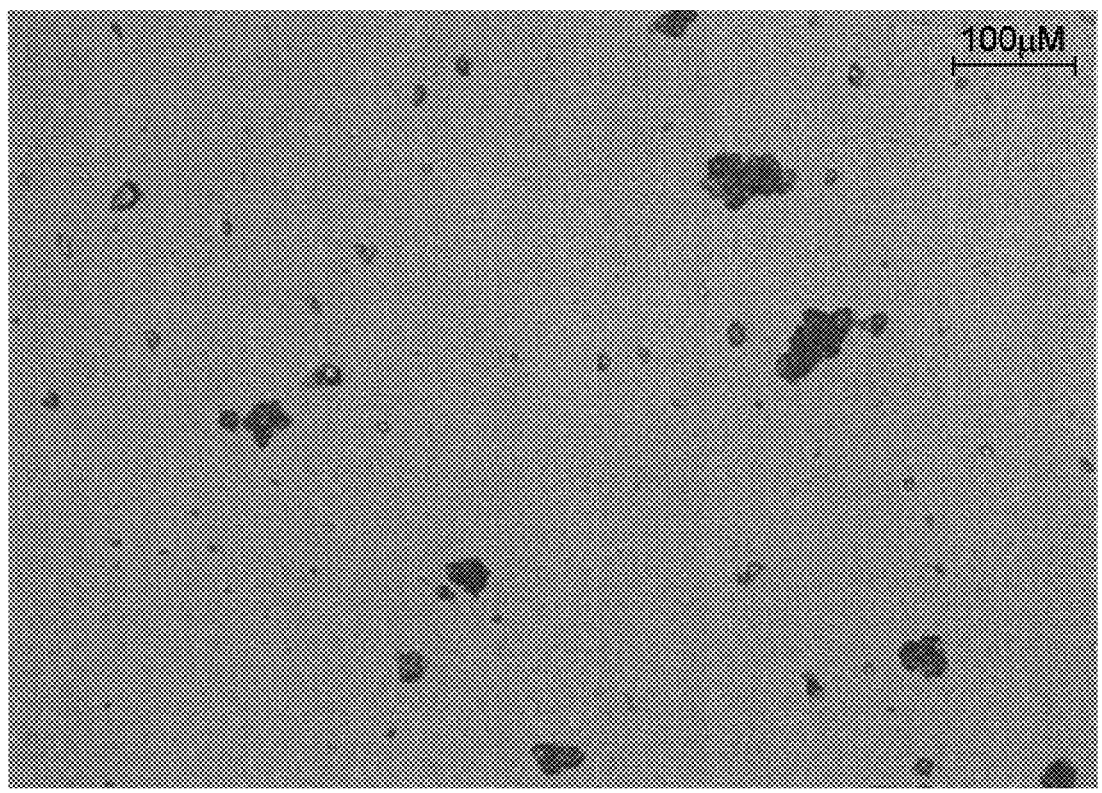
FIG. 15 is a microphotograph of E6070 crystals.

A 1 g scale of crystalline E6070 was prepared using mechanical stirring to check crystal form and size for the scale-up. The XRD pattern of this lot was same as previous lots and the TG thermogram indicated that the water content is consistent with the trihydrate theoretical value, i.e. 10.0%. This showed that crystalline E6070 prepared on gram scale was the same crystal form as those described in the Examples above. FIG. 15 is a photomicrograph of E6070 crystals from this 1 g scale crystallization. The largest crystal size looked to be less than 100 µm.

EXAMPLE 10

Milling of Crystalline E6070

The color of crystalline E6070 depends upon and changes with its particle size. This was demonstrated when a single lot of E6070 was micronized at Hosakawa Micron Powder Systems, which was contracted for the milling operations. Five test runs were milled as shown in Table 9, where "d(0.5)" indicates that 50% of the sample had that particle size or less and "d(0.9)" indicated that 90% of the sample had that particle size or less. In these runs there was a visible difference between runs 2 and 3, and runs 4 and 51-5 in which the yellow tone of samples increased as the average particle size decreased.

TABLE 10

Milling of Crystalline E6070

| Run # | RPM | d(0.5) | d(0.9) | Color |
|---|---|---|---|---|
| 1 | 10000 | 28.2 | 58.43 | yellow |
| 2 | 7000 | 40.14 | 99.08 | |
| 3 | 6000 | 45.74 | 96.98 | |
| 4 | 5000 | 80.17 | 187.62 | |
| 5 | 5000 | 95.91 | 190.92 | orange-yellow/peach |

EXAMPLE 11

Solid-State $^{13}$C NMR Spectrum of Crystalline E6070

Figure 16:
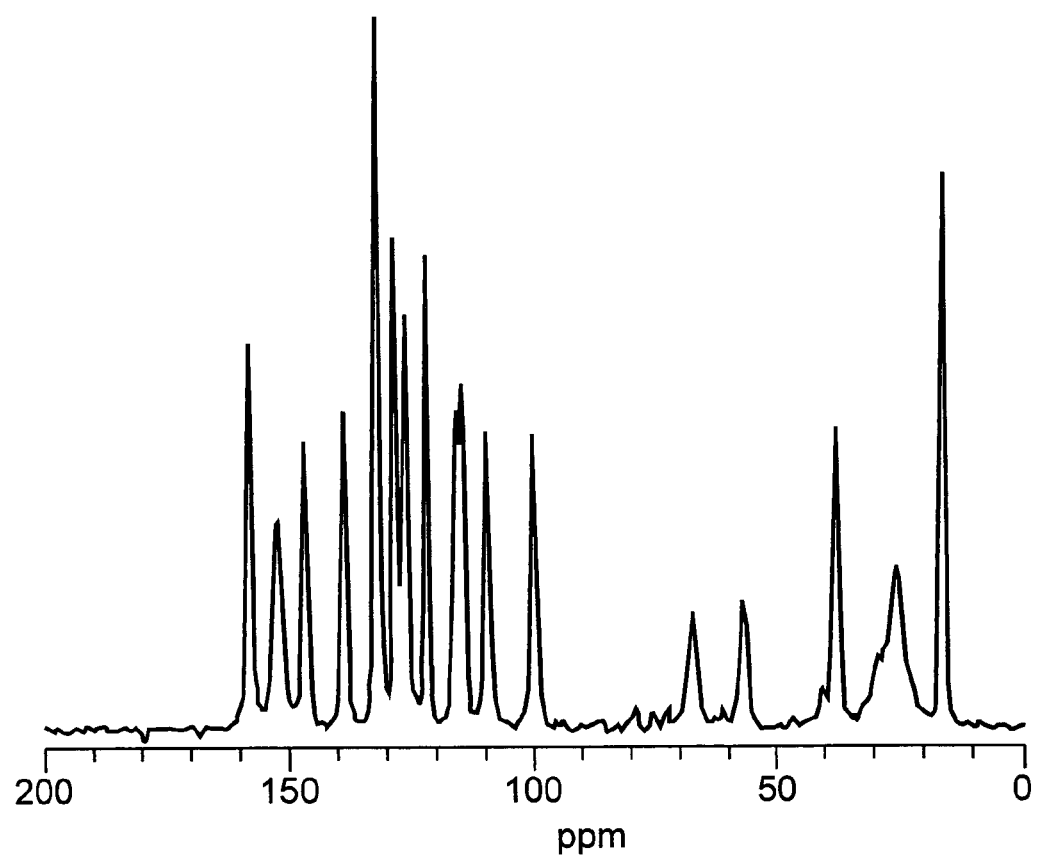
FIG. 16 is a solid state $^{13}C$ NMR spectrum of crystalline E6070.

To obtain a solid-state $^{13}$C NMR spectrum of crystalline E6070, a 7.5-mm rotor was packed with crystalline E6070 powder. The spectrum was recorded on a Chemagnetics CMX-II 300 NMR spectrometer operating at 75.3 MHz for $^{13}$C. The $^{13}$C NMR spectrum was acquired using CPMAS (cross-polarization magic-angle spinning) and total side band suppression (TOSS). The rotor was spun at the magic angle at a rate of 4 kHz. Variable-amplitude cross polarization (VACP) and two-pulse phase modulation (TPPM) were also used to obtain the spectrum. The $^1$H 90° pulse width was 4.2 µs, and the $^{13}$C 180° pulse width was 8.4 µs. 2048 points were acquired using a spectral width of 30.03 kHz, corresponding to a data acquisition time of 68 ms. The spectrum was acquired using a contact time of 1 ms, and a repetition time between pulses of 5 s. A total of 16384 transients were averaged to obtain the spectrum. Chemical shifts were assigned using the methyl peak of hexamethylbenzene as an external reference, with the methyl peak having a chemical shift value of 17.35 ppm. The solid-state $^{13}$C NMR spectrum of crystalline E6070 is shown in FIG. 16. As shown in the spectrum, characteristic peaks for crystalline E6070 appear at 16.1; 25.5; 37.8; 57.1; 67.2; 67.4; 100.2; 109.9; 114.8; 115.9; 121.9; 126.2; 128.3; 131.7; 138.8; 146.9; 152.3; and 158.0 ppm. Chemical shifts are reported to be within ±0.3 ppm.

Preferred characteristic peaks for the identification of crystalline E6070 can be found in the region of approximately 120-160 ppm. In general, these preferred peaks can be observed in the solid-state $^{13}$C NMR spectrum of an intact tablet without significant overlap from other peaks. The reason is that many common excipients, which are the ingredients added to the active pharmaceutical ingredient (API) to make the pharmaceutical tablet composition, will also show up in the solid-state $^{13}$C NMR spectrum. Given their chemical nature, the resonances for these excipients generally appear between 50 and 110 ppm in the $^{13}$C NMR spectrum. The excipient peaks can be significantly more intense than the peaks from the API if the tablet composition is dominated by excipients. In addition, excipient peaks may also occur in the aliphatic region (0-50 ppm) and in the carbonyl region (160-190 ppm) region. However, it is rare for an excipient peak to be located between 120-160 ppm. For this reason the preferred range in the solid-state $^{13}$C NMR spectra to identify and compare peaks from an active ingredient is 120-160 ppm. Crystalline E6070 according to the invention is preferably characterized by having at least two peaks in the solid state $^{13}$C NMR spectrum selected from 121.9±0.3 ppm; 126.2±0.3 ppm; 128.3±0.3 ppm; 131.7±0.3 ppm; 138.8±0.3 ppm; 146.9±0.3 ppm; 152.3±0.3 ppm; and 158.0±0.3 ppm.

The claimed invention is:

1. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate.

2. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate of claim 1, characterized by having at least two peaks in the powder X-ray diffraction pattern selected from the group consisting of 8.3±0.2° 2Θ, 10.1±0.2° 2Θ, 14.3±0.2° 2Θ, 15.3±0.2° 2Θ, and 18.1±0.2° 2Θ.

3. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate of claim 1, having a monoclinic crystal system and a P2$_1$/n space group.

4. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate of claim 3 characterized by crystal lattice parameters of:
a=16.915(3) Å
b=12.384(2) Å
c=12.554(2) Å
β=97.089(8)°
V=2609.7(9) Å$^3$
and having a Z value=4.

5. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate of claim 1, characterized by having at least two peaks in the solid state $^{13}$C NMR spectrum selected from the group consisting of 121.9±0.3 ppm; 126.2±0.3 ppm; 128.3±0.3 ppm; 131.7±0.3 ppm; 138.8±0.3 ppm; 146.9±0.3 ppm; 152.3±0.3 ppm; and 158.0±0.3 ppm.

6. Crystalline 1H-Imidazo[4,5-b]pyridin-5-amine, 7-[5-[(cyclohexylmethylamino)-methyl]-1H-indol-2-yl]-2-methyl, sulfate (1:1), trihydrate of claim 1, characterized by having at least two absorption bands in an infrared spectrum of a neat sample selected from the group consisting of 1656, 1620, 1549, 1136, 1085, and 1033 cm$^{-1}$.

7. A pharmaceutical composition comprising crystalline 1H-Imidazo[4,5-b]pyridin-5-amine, 7-[5-[(cyclohexylmethylamino)-methyl]-1H-indol-2-yl]-2-methyl, sulfate (1:1), trihydrate and a pharmaceutically acceptable carrier.

8. A pharmaceutical composition of claim 7 wherein the crystalline 1H-Imidazo[4,5-b]pyridin-5-amine, 7-[5-[(cyclohexylmethylamino)-methyl]-1H-indol-2-yl]-2-methyl, sulfate (1:1), trihydrate is characterized by having at least two peaks in the powder X-ray diffraction pattern selected from the group consisting of 8.3±0.2° 2Θ, 10.1±0.2° 2Θ, 14.3±0.2° 2Θ, 15.3±0.2° 2Θ, 18.1±0.2° 2Θ, 21.1±0.2° 2Θ, 24.1±0.2° 2Θ, and 29.2±0.2° 2Θ.

9. A pharmaceutical composition of claim 7 wherein the crystalline 1H-Imidazo[4,5-b]pyridin-5-amine, 7-[5-[(cyclohexylmethylamino)-methyl]-1H-indol-2-yl]-2-methyl, sulfate (1:1), trihydrate has a monoclinic crystal system and a P2$_1$/n space group.

10. A pharmaceutical composition of claim 9 wherein the crystalline 1H-Imidazo[4,5-b]pyridin-5-amine, 7-[5-[(cyclohexylmethylamino)-methyl]-1H-indol-2-yl]-2-methyl, sulfate (1:1), trihydrate is characterized by crystal lattice parameters of:
a=16.915(3) Å
b=12.384(2) Å
c=12.554(2) Å
β=97.089(8)°
V=2609.7(9) Å$^3$
and having a Z value=4.

11. A pharmaceutical composition of claim 7 wherein the crystalline 1H-Imidazo[4,5-b]pyridin-5-amine, 7-[5-[(cyclohexylmethylamino)-methyl]-1H-indol-2-yl]-2-methyl, sulfate (1:1), trihydrate is characterized by having at least two peaks in the solid state $^{13}$C NMR spectrum selected from the group consisting of 121.9±0.3 ppm; 126.2±0.3 ppm; 128.3±0.3 ppm; 131.7±0.3 ppm; 138.8±0.3 ppm; 146.9±0.3 ppm; 152.3±0.3 ppm; and 158.0±0.3 ppm.

12. A pharmaceutical composition of claim 7 wherein the crystalline 1H-Imidazo[4,5-b]pyridin-5-amine, 7-[5-[(cyclohexylmethylamino)-methyl]-1H-indol-2-yl]-2-methyl, sulfate (1:1), trihydrate is characterized by having at least two absorption bands in an infrared spectrum of a neat sample selected from the group consisting of 1656, 1620, 1549, 1136, 1085, and 1033 cm$^{-1}$.

13. A method for the preparation of crystalline 1H-Imidazo [4,5-b]pyridin-5-amine, 7-[5-[(cyclohexylmethylamino)-methyl]-1H-indol-2-yl]-2-methyl, sulfate (1:1), trihydrate, E6070, according to the reaction

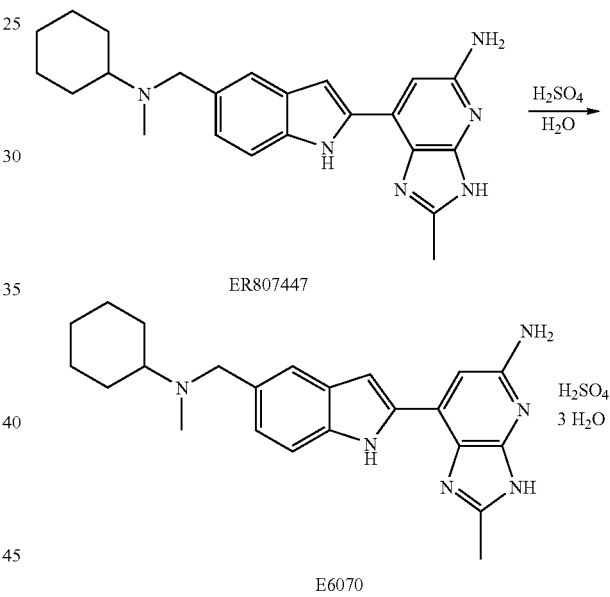

comprising the steps of:
suspending ER807447 in water to form an aqueous suspension;
adding H$_2$SO$_4$ to the aqueous suspension to form a solution while keeping the internal temperature of the solution below 25° C.,
optionally filtering the solution, and
slowly warming the aqueous solution until E6070 crystallizes from solution.

14. A method of claim 13, further comprising, before the warming step, the step of adding a seed crystal of E6070 to the solution.

15. A method of claim 14, wherein the warming steps comprises slowly warming the solution to about 70° C. over about 2.5 h.

16. A method of claim 13, wherein the warming steps comprises slowly warming the solution to about 70° C. over about 2.5 h.

* * * * *